US00PP23556P3

(12) United States Plant Patent
Meilland

(10) Patent No.: US PP23,556 P3
(45) Date of Patent: Apr. 23, 2013

(54) FLORIBUNDA ROSE PLANT NAMED 'MEIMASULA'

(50) Latin Name: *Rosa hybrida*
Varietal Denomination: Meimasula

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 13/137,455

(22) Filed: Aug. 17, 2011

(65) Prior Publication Data

US 2013/0047304 P1 Feb. 21, 2013

(51) Int. Cl.
*A01H 5/00* (2006.01)

(52) U.S. Cl. ..... Plt./142

(58) Field of Classification Search ..... Plt./142
See application file for complete search history.

*Primary Examiner* — Kent L Bell

(74) *Attorney, Agent, or Firm* — Buchanan Ingersoll & Rooney

(57) ABSTRACT

A new and distinct variety of Floribunda rose plant is provided that abundantly forms on a substantially continuous basis attractive semi-double intense red blossoms having a darker smoked-red margin and a white eye. The vegetation is strong and a somewhat creeping growth habit is displayed. The plant lacks thorns during observations to date. Good tolerance to common diseases and pests is exhibited. The plant is particularly well suited for providing distinctive attractive ornamentation in the landscape.

1 Drawing Sheet

Botanical/commercial classification: *Rosa hybrida*/Floribunda Rose Plant.

Varietal denomination: cv. Meimasula.

SUMMARY OF THE INVENTION

The new variety of *Rosa hybrida* Floribunda rose plant was created in France by artificial pollination wherein two parents were crossed which previously had been studied in the hope that they would contribute the desired characteristics. The female parent (i.e., the seed parent) was the 'Kormax' variety (non-patented in the United States). The male parent (i.e., the pollen parent) was the product of the cross of the 'Meikrotal' variety (U.S. Plant Pat. No. 6,087) and 'Noacas' variety (non-patented in the United States). The parentage of the new variety can be summarized as follows:

'Kormax'×('Meikrotal'×'Noacas').

The seeds resulting from the above pollination were sown and small plants were obtained which were physically and biologically different from each other. Selective study resulted in the identification of a single plant of the new variety.

It was found that the new Floribunda rose plant of the present invention:

(a) forms strong vegetation,
(b) forms a somewhat creeping growth habit,
(c) forms in abundance on a substantially continuous basis attractive semi-double intense red blossoms having a darker smoked-red margin and a white eye,
(d) displays attractive dark green foliage with a glossy aspect on the upper surface,
(e) lacks thorns during observations to date,
(f) exhibits good tolerance to common diseases and pests, and
(g) is particularly well suited for providing distinctive attractive ornamentation in the landscape.

The new variety well meets the needs of the horticultural industry and can be grown to advantage in parks and gardens.

The new variety can be readily distinguished from its ancestors. The male parent is non-patented and unnamed and has not been released to the public. The blossoms of the male parent are uniform bright red in coloration and possess only 5 petals unlike the new variety. For instance, 'Kormax' variety forms large red blossoms having only six petals. The 'Meikrotal' variety forms blossoms that are cherry red on the upper surface and carmine pink on the under surface and commonly bears more petals than the new variety. The 'Noacas' variety forms dissimilar orange to orange-red blossoms of a more uniform coloration.

The new variety has been found to undergo asexual propagation at Le Cannet des Maures, Var, France, by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meimasula'.

BRIEF DESCRIPTION OF THE PHOTOGRAPH

The accompanying photograph shows as nearly true as it is reasonably possible to make the same in a color illustration of this character, typical specimens of plant parts of the new variety. The rose plants of the new variety were approximately five years of age and were observed during June while budded on *Rosa froebelli* understock and growing outdoors at Le Cannet des Maures, Var, France. Standard colors are presented at the bottom of the photograph for comparison.

FIG. 3 illustrates a specimen of a floral bud at the further opening of the sepals;

FIG. 4 illustrates a specimen of a floral bud at the opening of the petals;

FIG. 5 illustrates a specimen of a flower in the course of opening;

DETAILED DESCRIPTION

Figures 1, 2, 6, 7, 8, 9, 10, 11, 12, 13, 14, 15, 16, 17:
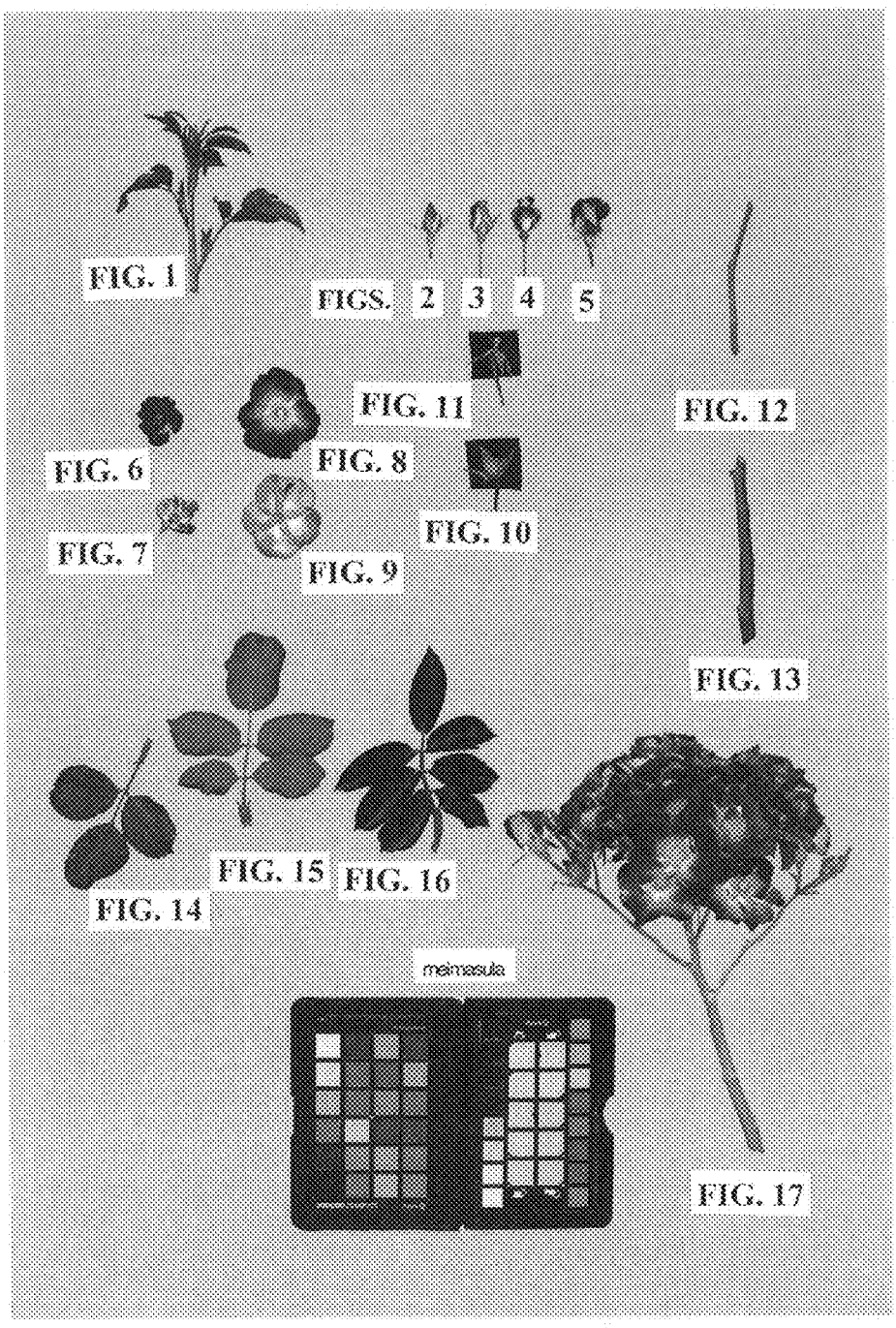
FIG. 1 illustrates a specimen of a young shoot.
FIG. 2 illustrates a specimen of a floral bud soon after the opening of the sepals.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing arrangement of the stamens and pistils.
FIG. 11 illustrates a specimen of a floral receptacle showing arrangement of the pistils (stamens removed)
FIG. 12 illustrates a specimen of a flowering stem which is lacking thorns.
FIG. 13 illustrates a specimen of a main branch which is lacking thorns.
FIG. 14 illustrates a specimen of a leaf with 3 leaflets—plan view—upper surface.
FIG. 15 illustrates a specimen of a leaf with 5 leaflets—plan view—under surface.
FIG. 16 illustrates a specimen of a leaf with 7 leaflets—plan view—upper surface.
FIG. 17 illustrates a specimen of a cluster of buds, flowers in the course of opening, and fully open flowers.

The chart used in the identification of the colors is that of The Royal Horticultural Society (R.H.S. Colour Chart) except where ordinary color terms are utilized. Such common color terms are to be accorded their customary dictionary significance. The description is based upon the observation during June of plants of the new variety at an age of approximately five years while budded on *Rosa froebelli* rootstock and growing outdoors at Le Cannet des Maures, Var, France.

Class: Floribunda.

Plant:

*Growth habit*.—Somewhat creeping.

*Height*.—Commonly approximately 80 cm on average.

*Width*.—Commonly approximately 70 cm on average.

Branches:

*Color*.—Young stems: near Green Group 138B. Adult wood: near Yellow-Green Group 146D.

*Texture*.—Smooth for young and adult branches.

*Thorns*.—Not formed during observations to date.

Leaves:

*Overall appearance*.—Very dense, attractive dark green.

*Size*.—Commonly approximately 4 cm in length on average and approximately 2.8 cm in width on average for a typical five-leaflet leaf.

*Leaflets*.—Shape: generally ellliptic. Number: 3, 5 and 7 (most often). apex: acuminate. base: obtuse. Size: the terminal leaflets commonly are approximately 4.5 cm in length on average, and approximately 2.8 cm in width on average. Serration: small and single. Texture: firm and leathery. Color: young foliage: near Green Group 137A on the upper surface, and near Yellow-Green Group 147B on the under surface. mature foliage: near Yellow-Green Group 147A on the upper surface, and near Yellow-Green Group 147B on the under surface.

*Stipules*.—General appearance: adnate, pectinate, and rather broad. Texture: smooth. Length: approximately 1.5 cm on average. Width: approximately 0.6 cm on average. Color near Yellow-Green Group 147C on the upper and under surfaces.

*Petioles*.—Length: commonly approximately 2.5 cm on average for the terminal leaflet. Diameter: commonly approximately 0.2 cm on average. Texture: non-glandular on the upper surface, and commonly without prickles on the under surface. Color near Yellow-Green Group 147B on the upper surface, and near Yellow-green Group 147C on the under surface.

*Rachis*.—Length: commonly approximately 0.5 cm on average. Diameter commonly approximately 0.2 cm on average. Texture: smooth. Color near Yellow-Green Group 147B on the upper surface, and near Yellow-Green Group 147C on the under surface.

Inflorescence:

*Number of flowers*.—Commonly three to five or more per stem.

*Peduncle*.—Approximately 3 cm in length on average, approximately 2 mm in diameter on average, smooth in texture, and commonly near Yellow-Green Group 147C in coloration.

*Sepals*.—Generally obovate, narrow-pointed tip, relatively smooth margins, tomentose on upper surface, smooth on under surface, generally upright at the base, commonly with convex tips, commonly approximately 1.3 cm in length on average, approximately 0.7 cm in width on average at the widest point, near Yellow-Green Group 147C on the upper surface, and near Yellow-Green Group 147 suffused with near Yellow-Green Group 148A on the under surface.

*Buds*.—Shape: generally conical. Size: small. Length: approximately 1 cm on average. Width: approximately 1 cm at the widest point on average. Color: upper surface: near Red Group 46A suffused with near Red Group 53A. under surface: on the external petals near Red Group 53A, and on the inner petals near White Group 155D amply suffused with near Red Group 54B and Red Group 54C.

*Flower*.—Diameter approximately 5 cm on average when fully open. Height: commonly approximately 2 cm on average. Shape: cup-shaped. Color (in course of opening): upper side: near Red Group 45B amply suffused with near Red Group 46A and with a spot of White Group 155D at the base. under side: near Red-Purple Group 62B slightly suffused with near Red-Purple Group 58B and with a spot of White Group 155D at the base. Color (when fully open): upper side: with a white eye at the base near White Group 155D, thereafter intense red near Red-Purple Group 62D suffused with Red-Purple Group 58B and amply suffused with Red Group 46A, and at the extreme margin near Brown Group 200A. under side: with a white eye at the base near White Group 155D, and thereafter near Red-Purple Group 62D amply suffused with near Red-Purple Group 62B and Red-Purple Group 62C, and more or less margined with near Red Group 54A. Fragrance: none observed. Petal number commonly approximately 14 on average under normal growing conditions. Petal shape: generally obovate, with a rounded tip and a cuneiform base and reflexed margins. Petal size: commonly approximately 2.7 cm on average in length and width. Petal arrangement: imbricated and without petaloids. Petal substance: firm and leathery. Petal drop: good with the petals commonly detaching cleanly before drying. Stamen number: approximately 86 on average. Anthers: regularly arranged around the styles, approximately 2 mm in length on average, approximately 1 mm in width on average, and near Yellow-Orange Group 22C in coloration. Filaments: commonly approximately 2 mm in length on average, approximately 1 mm in diameter on average, and near Red Group 42D in coloration. Pollen: commonly present in a moderate quantity and near Yellow-Orange Group 22C in coloration. Pistils: commonly approximately 31 on average. Styles: approximately 1 mm in length on average, and commonly near Yellow Group 8D in coloration. Stigmas: commonly approximately 3 mm in diameter on average, and commonly near Yellow Group 8D in coloration. Receptacle: shape: pitcher-shaped. length: approximately 6 mm on average. width: approximately 5 mm at widest point on average. texture: smooth. color. near Yellow-Green Group 147C. Hips: substantially round in configuration, approximately 1 mm in diameter on average, and commonly near Orange-Red Group 33B in coloration.

Development:

*Vegetation*.—Strong.

*Blooming*.—Medium season, very abundant, and substantially continuous.

*Tolerance to diseases*.—Very good for common diseases.

*Tolerance to pests*.—Very good for common pests.

Plants of the new 'Meimasula' variety have not been observed under all possible environmental conditions to date. Accordingly, it is possible that the phenotypic expression may vary somewhat with changes in light intensity and duration, cultural practices, and other environmental conditions.

I claim:

1. A new and distinct Floribunda rose plant characterized by the following characteristics:

(a) forms strong vegetation, (b) forms a somewhat creeping growth habit, (c) forms in abundance on a substantially continuous basis attractive semi-double intense red blossoms having a darker smoked-red margin and a white eye, (d) displays attractive dark green foliage with a glossy aspect on the upper surface, (e) lacks thorns during observations to date, (f) exhibits good tolerance to common diseases and pests, and (g) is particularly well suited for providing distinctive attractive ornamentation in the landscape;

substantially as shown and described.

* * * * * meimasula